United States Patent
Cho (10) Patent No.: US 11,337,820 B2
(45) Date of Patent: May 24, 2022

(54) METHOD, SYSTEM, AND APPARATUS FOR PRODUCING IN INTERBODY IMPLANTS

(71) Applicant: Samuel Cho, Englewood Cliffs, NJ (US)

(72) Inventor: Samuel Cho, Englewood Cliffs, NJ (US)

( * ) Notice: Subject to any disclaimer, the term of this patent is extended or adjusted under 35 U.S.C. 154(b) by 0 days.

(21) Appl. No.: 17/030,348

(22) Filed: Sep. 23, 2020

(65) Prior Publication Data

US 2021/0085472 A1     Mar. 25, 2021

Related U.S. Application Data

(60) Provisional application No. 62/912,405, filed on Oct. 8, 2019, provisional application No. 62/904,983, filed on Sep. 24, 2019.

(51) Int. Cl.
*A61F 2/30* (2006.01)
*A61F 2/44* (2006.01)

(52) U.S. Cl.
CPC .......... *A61F 2/30942* (2013.01); *A61F 2/442* (2013.01); *A61F 2002/30301* (2013.01); *A61F 2002/30622* (2013.01); *A61F 2002/30948* (2013.01); *A61F 2002/443* (2013.01)

(58) Field of Classification Search
CPC .... A61F 2/30942; A61F 2/442; A61F 2/4425; A61F 2002/30301; A61F 2002/30622; A61F 2002/30948; A61F 2002/443
See application file for complete search history.

(56) References Cited

U.S. PATENT DOCUMENTS

2016/0270931 A1*  9/2016  Trieu ............... A61F 2/30942
2017/0252107 A1*  9/2017  Turner ............... A61B 34/10

* cited by examiner

*Primary Examiner* — Zade Coley
*Assistant Examiner* — Diana Jones
(74) *Attorney, Agent, or Firm* — Merle W. Richman, Esq.

(57) ABSTRACT

Embodiments of forming custom interbody implants that may be used to stabilize region(s) formed between mammalian bony segments, including systems and methods to produce a custom interbody element that may be used to stabilize or couple region(s) formed between two or more mammalian bony segments. Other embodiments may be described and claimed.

19 Claims, 9 Drawing Sheets

AREA BB

METHOD, SYSTEM, AND APPARATUS FOR PRODUCING IN INTERBODY IMPLANTS

TECHNICAL FIELD

Various embodiments described herein relate generally to stabilizing mammalian bony segments, including systems and methods to produce an interbody element to stabilize or couple one or more mammalian bony segments.

BACKGROUND INFORMATION

It may be desirable to stabilize or couple one or more bony segments via an interbody element, the present invention provides methods, systems, and apparatus for producing such an interbody element that may be customized for the bony segments and the desired mobility between the bony segments.

DETAILED DESCRIPTION

It may be desirable to fixably or moveably couple one or more bony regions or segments to enable the regions therebetween to become fixably or movably stabilized, joined, or fused together. In an embodiment, the bony segments may be separated by one or more non-bony elements, for example the bony segments 10 may be vertebra separated by spinal discs in a cervical, thoracic, or lumbar region of a mammal including a human. In another embodiment, the bony segments may be part of a single, fractured bone to be stabilized such a femur or other long mammalian bone.

For each application the region to be stabilized between bony regions or segments may vary as each person's anatomy is unique, including the size, shape, and attributes (desired controlled movement between bony regions including translating movement, rotational movement, and pivotable movement). The desired controlled movement between two bony regions may include a plurality of degrees of motion including six degrees of motion in an embodiment. Producing a plurality of preformed interbody implants with limited sizes, shapes, and desired controlled movement may make selection, insertion, and placement of the performed interbody implants difficult for a surgeon. In addition, the resultant implantation may yield a non-ideal bony region stabilization as a surgeon may be required to compromise location and position due to limited sizing, shapes, and desired controlled movement (when not fixed).

Figure 1A:
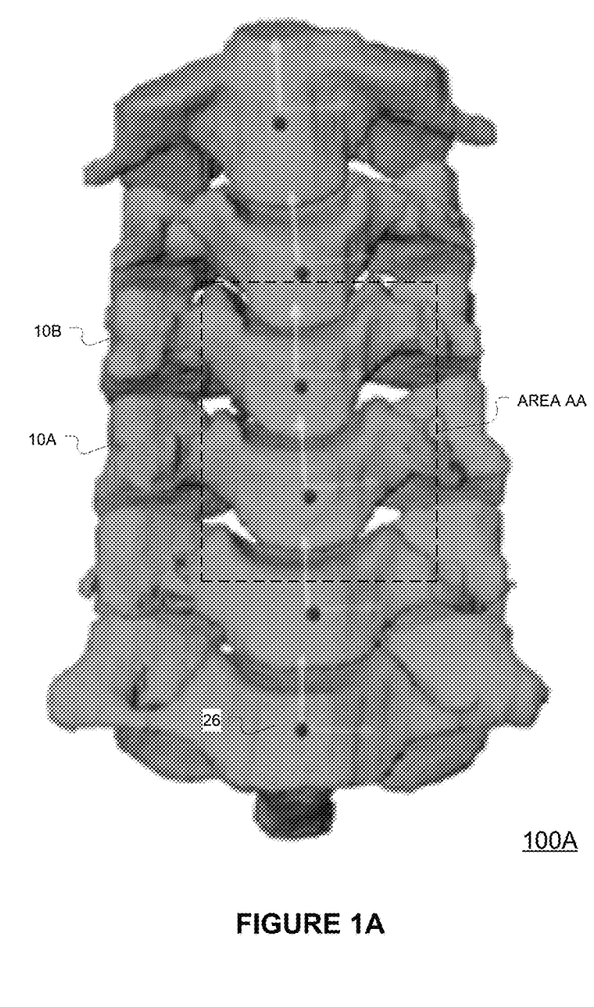
FIG. 1A is a simplified, anterior view drawing of a plurality of cervical vertebrae according to various embodiments.
Figure 1B:
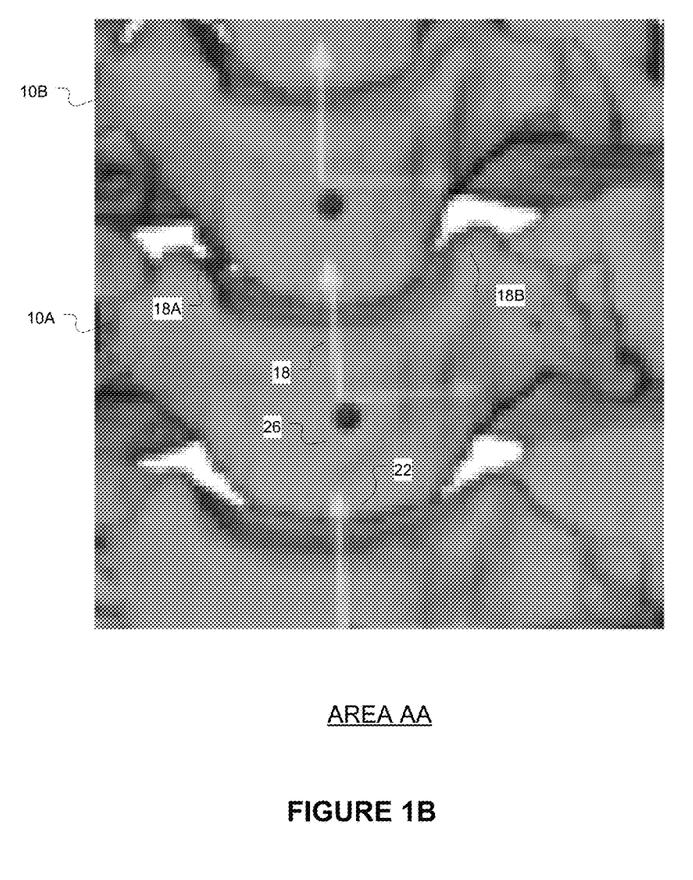
FIG. 1B is an enlarged drawing of area AA of FIG. 1A according to various embodiments.
Figure 1C:
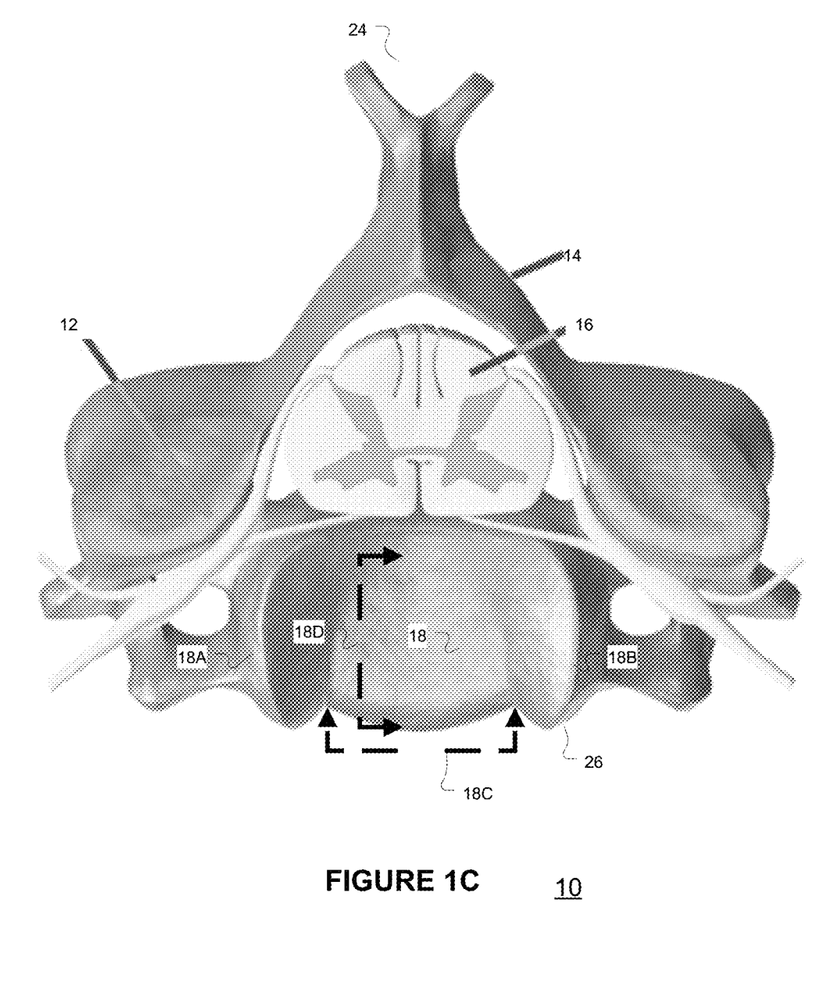
FIG. 1C is a simplified, superior view drawing of a cervical vertebrae according to various embodiments.

FIG. 1A is a simplified, anterior view drawing 100A of a plurality of human cervical vertebrae 10 including two adjacent vertebrae 10A (inferior), 10B (superior) according to various embodiments. FIG. 1B is an enlarged drawing of area AA of FIG. 1A according to various embodiments. FIG. 1C is a simplified, superior view drawing of a cervical vertebrae 10 according to various embodiments. As shown in these figures, a cervical vertebrae 10 anterior, upper region 18 may have a saddle shape with a left arm 18A and a right arm 18B. A cervical vertebrae 10 anterior, lower region 22 may have a box type shape with a left side 22A and a right side 22B (shown in FIG. 2C).

Figure 2A:
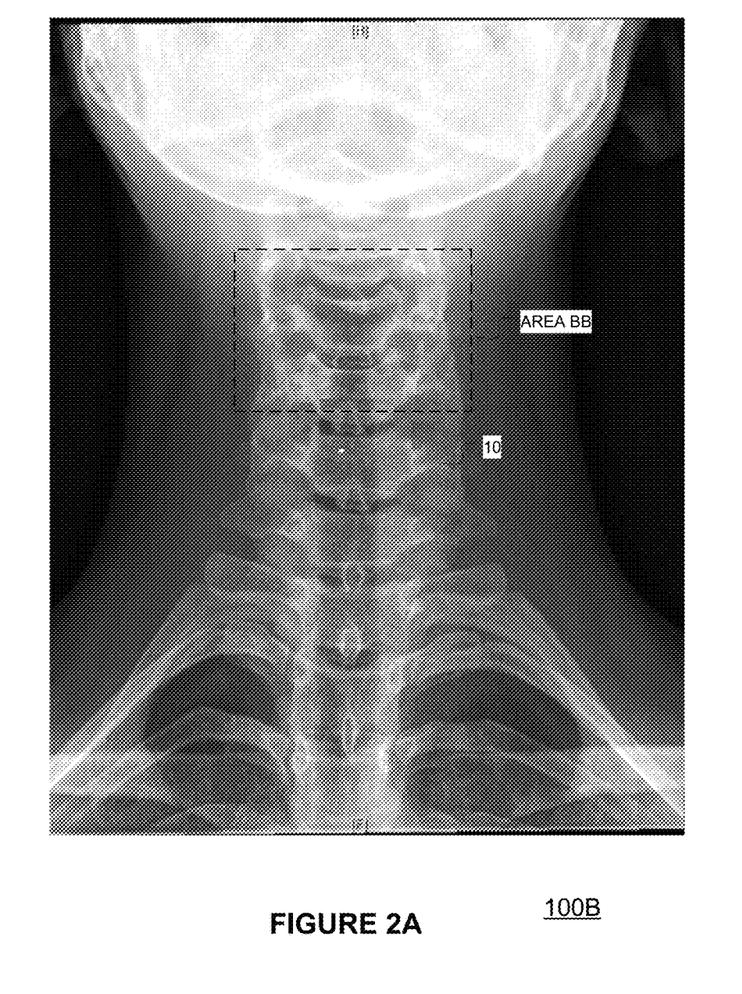
FIG. 2A is an anterior x-ray image of a plurality of cervical vertebrae according to various embodiments.
Figure 2B:
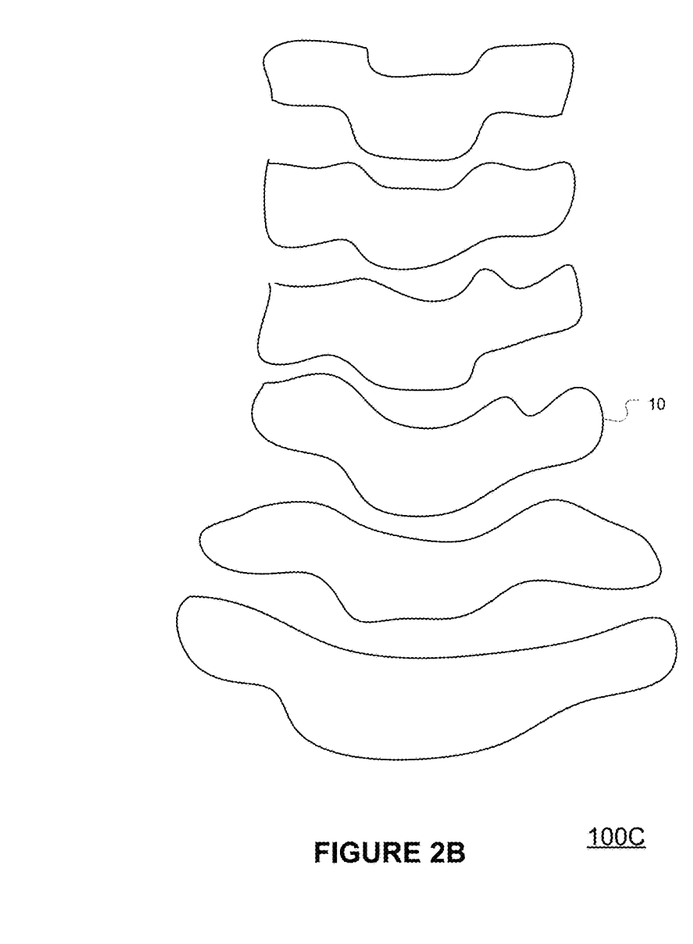
FIG. 2B are simplified models of the plurality of cervical vertebrae shown in FIG. 2A according to various embodiments.
Figure 2C:
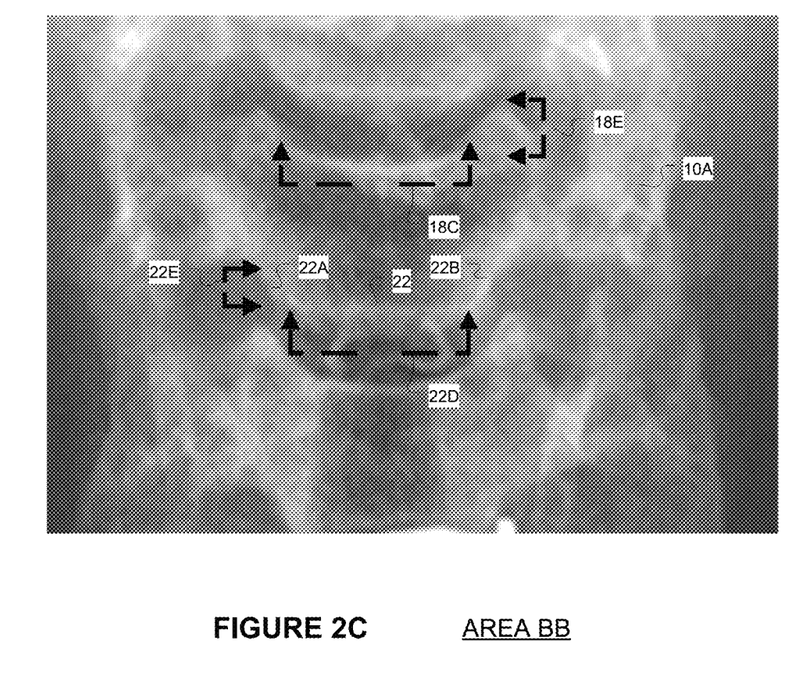
FIG. 2C is an enlarged x-ray image of area BB with annotations of FIG. 2A according to various embodiments.

FIG. 2A is an anterior view x-ray image 100B of a plurality of adjacent cervical vertebrae 10 according to various embodiments. FIG. 2C is an enlarged image of area BB with annotations of FIG. 2A according to various embodiments. FIGS. 5A-5E are simplified, lateral view drawings 100A of a plurality of adjacent cervical vertebrae 10 in different states of extension and flexion according to various embodiments. FIGS. 6A-6E are simplified, anterior view drawings 100A of a plurality of adjacent cervical vertebrae 10 in different states of extension, flexion, and lateral flexion according to various embodiments.

As shown in these figures the upper region 18 of an inferior cervical vertebrae 10A may form a relief for the lower region 22 of a superior cervical vertebrae 10B (for the adjacent, cervical vertebrae 10A, 10B). As also shown in these figures, the size and shape of the region formed between an inferior cervical vertebrae 10A upper region 18 and a superior cervical vertebrae 10B lower region 22 varies by cervical vertebrae 10 level and state of movement between them including extension flexion, lateral flexion, and rotation of the cervical vertebrae 10 (which varies each person' anatomy and state of mobility of their cervical spine).

Figure 8:
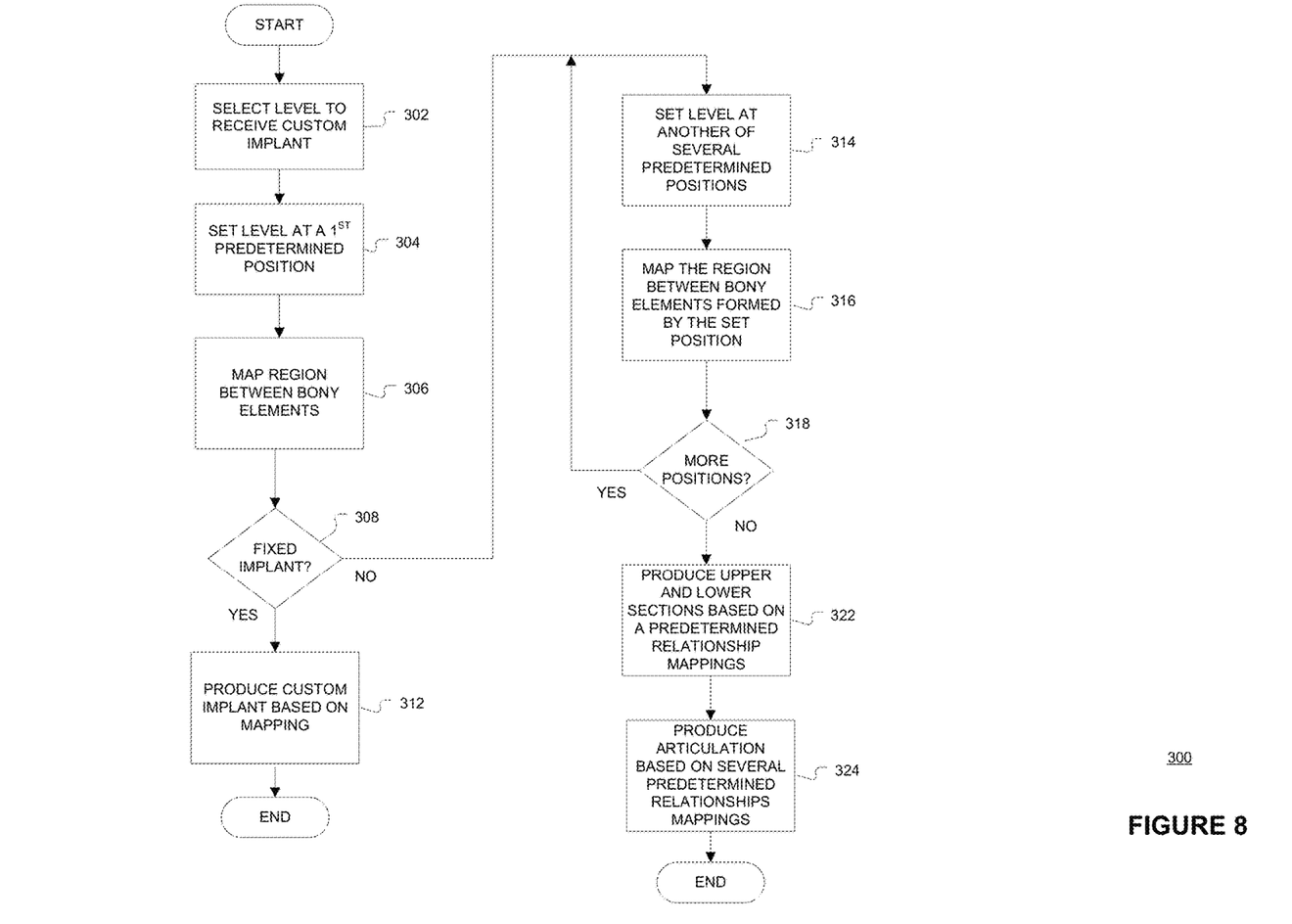
FIG. 8 is a flow diagram illustrating mammalian bony segment custom interbody formation algorithms according to various embodiments.

In an embodiment, custom interbody implants 100A-C are produced for each patient and region to be stabilized via mappings of various states of the region(s) to be stabilized, e.g. mapping of the region between adjacent vertebrae 10A, 10B during various states of extension, flexion, lateral flexion, and rotation may be taken for a individual. FIG. 2B are simplified models of the plurality of adjacent cervical vertebrae 10 shown in FIG. 2A according to various embodiments that may be formed by a mapping activity in an embodiment. In an embodiment, a custom interbody implant may be formed based on exact mappings via various manufacturing techniques and materials. FIG. 8 is a flow diagram illustrating mammalian bony segment custom interbody formation algorithms 300 according to various embodiments. In an embodiment, a technician, surgeon, or other medical professional may select a region formed between two adjacent bony elements (such as adjacent vertebrae 10A, 10B) to be stabilized (activity 302).

In an embodiment, the technician, surgeon, or other medical professional may set the region to a neutral or first, predetermined position or relationship between the two adjacent bony elements by manipulating the position of the patient (activity 304) and thus the adjacent bony segments that form the region to be stabilized. In an embodiment, a neutral position between the bony elements may an non-elongated, non-rotated, and non-flexed state or position. For adjacent cervical vertebrae, neutral may have no elongation, flexion, lateral flexion, or rotation between the vertebrae. Then via various imaging technologies multiple view images of the region to be stabilized may be taken (activity 306) via various imaging systems including magnetic resolution imaging (MRI), ultrasound, optical camera (where region is exposed), computer tomography (CT). An anterior x-ray image 100B is shown in FIG. 2A. As noted, other images may be formed via x-ray, MRI, CT, ultrasound, optical camera (where region is exposed) to form a 2-D and 3-D model of the region.

In an embodiment, 4-D models may also be formed by placing the bony segments that form the region in various predetermined positions or relationships (states of motion) of a plurality of states of motion—such as full flexion non-rotated, no-limited lateral flexion, full extension, non-rotated, no-limited lateral flexion, full flexion full right-rotation, full extension, full right-rotation, full flexion full left-rotation, full extension, full left-rotation, no flexion non-rotated, no-limited lateral flexion, no extension, non-rotated, no-limited lateral flexion, no flexion full right-rotation, no extension, full right-rotation, no flexion full left-rotation, no extension, full left-rotation, partial flexion non-rotated, no-limited lateral flexion, partial extension, non-rotated, no-limited lateral flexion, partial flexion partial right-rotation, partial extension, partial right-rotation, partial flexion partial left-rotation, partial extension, partial left-rotation, no flexion non-rotated, no-limited lateral flexion, no extension, non-rotated, no-limited lateral flexion, no flexion partial right-rotation, no extension, partial right-rotation, no flexion partial left-rotation, no extension, partial left-rotation, partial flexion non-rotated, no-limited lateral flexion, partial extension, non-rotated, no-limited lateral flexion, partial flexion full right-rotation, partial extension, full right-rotation, partial flexion full left-rotation, partial extension, full left-rotation, among thousands of other predetermined relationships or positions between two, adjacent bony elements or vertebra 10A, 10B in an embodiment. In an embodiment, bony segments are moved relative to each other based on desired movement between the segments in embodiment such as in various degrees of extension and flexion for example as shown in FIGS. 5A-5E and 6A-6E).

Based on a first, predetermined position or relationship (neutral relationship in an embodiment) a mapping of the region's 3-D space (formed by the bony segments in said relationship) may be calculated, measured. or formulated (via various imaging systems including images formed by CT, x-ray, MRI, ultrasound, and optical camera and other imaging systems). For example, for region(s) formed between two cervical vertebrae 10, the width 22C, the depth 22D, and the height 22E of the superior cervical vertebrae 10 lower region 22 may be determined. In addition, the width 18C, the depth 18D, and the height 18E of the inferior cervical vertebrae 10 upper region 18 may be determined. The widths, depths, and heights 18C-18E and 22C-22E of the region formed at various predetermined positions or relationships may be calculated at a plurality of positions (of desired movement between the vertebra in an embodiment) to form a very precise model of the region(s) formed between bony segments.

In an embodiment, a custom fixed (non-moveable) interbody implant may be generated using various manufacturing techniques out of one or more biocompatible materials (activity 312). For example, the 3-D model may be provided to a multiple axis milling machine, 3-D printer (metal, alloy, or other) to product an implant of a biocompatible, metal, metal alloy, polymer, or combination thereof including titanium, stainless steel, ceramic, Polyetheretherketone (PEEK) or similar material, and others.

Figure 3A:
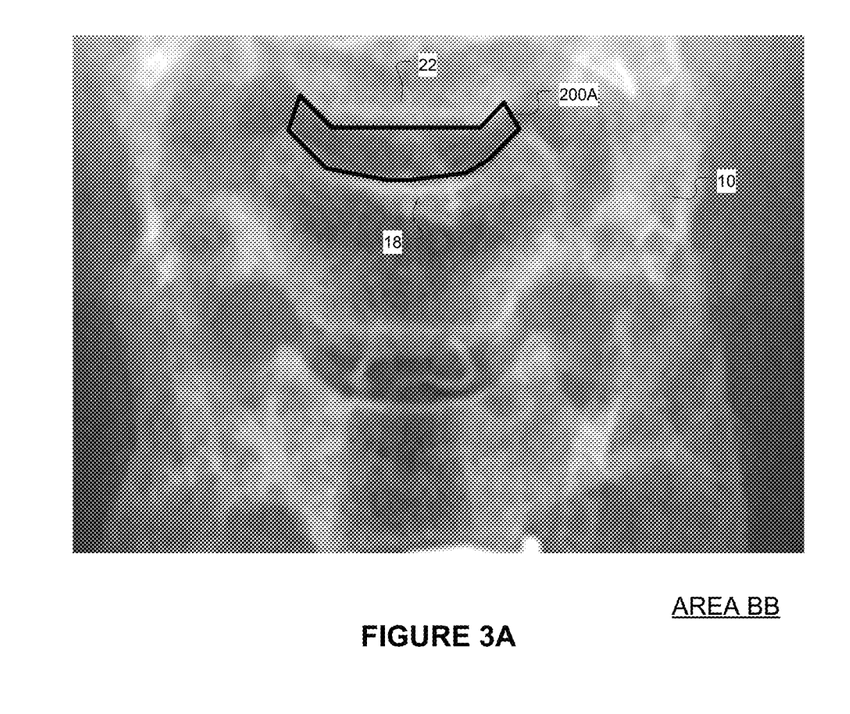
FIG. 3A is an enlarged x-ray image of area BB of FIG. 2A with a simplified drawing of a fixed custom interbody implant with elongated arms according to various embodiments.
Figure 3B:
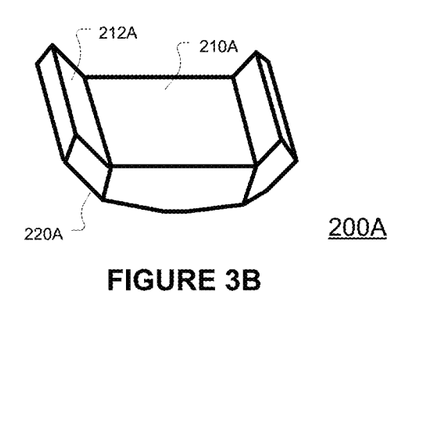
FIG. 3B is a simplified isometric drawing of a fixed custom interbody implant with elongated arms according to various embodiments.
Figure 3C:
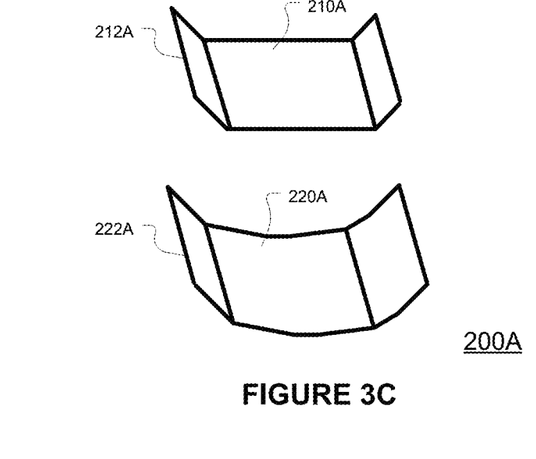
FIG. 3C is a simplified isometric drawing of top section and bottom section of a fixed custom interbody implant with elongated arms according to various embodiments.

FIG. 3A is an enlarged x-ray image of area BB of FIG. 2A with a simplified drawing of a fixed (non-moveable) custom interbody implant 200A with elongated arms 212A, 222A according to various embodiments. FIG. 3B is a simplified isometric drawing of the fixed custom interbody implant 200A with elongated arms 212A, 222A according to various embodiments. FIG. 3C is a simplified isometric drawing of top section 210A and bottom section 220B of a fixed custom interbody implant 200A with elongated arms 212A, 222A according to various embodiments. As shown in FIG. 3A, the interbody implant 200A may be sized to fit securely and precisely into the region formed between two, adjacent cervical vertebrae 10A. 10B for a predetermined relationship or position between them. In an embodiment, the predetermined relationship may a neutral position between the bony elements 10A, 10B. In an embodiment, the predetermined position may be non-neutral to correct various anatomical issues for the respective adjacent bony elements 10A, 10B. e.g. may have limited flexion, lateral flexion, extension, or rotation to correct relationship between vertebrae 10A, 10B or other vertebrae. The implants 200A arms 212A may engage the arms 18A, 18B of an inferior vertebrae 10A saddle 18 (upper region) and the sides 22A, 22B of a superior vertebrae 10B lower region 22 in an embodiment.

Figure 4A:
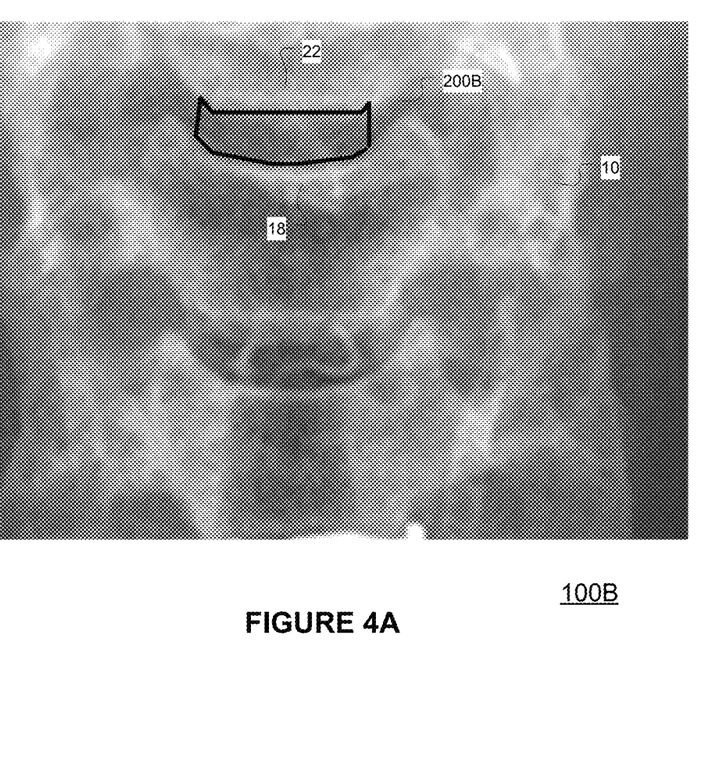
FIG. 4A is an enlarged x-ray image of area BB of FIG. 2A with a simplified drawing of a fixed custom interbody implant with shortened arms according to various embodiments.
Figure 4B:
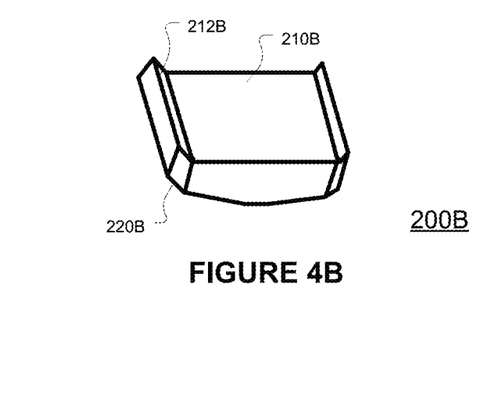
FIG. 4B is a simplified isometric drawing of a fixed custom interbody implant with shortened arms according to various embodiments.
Figure 4C:
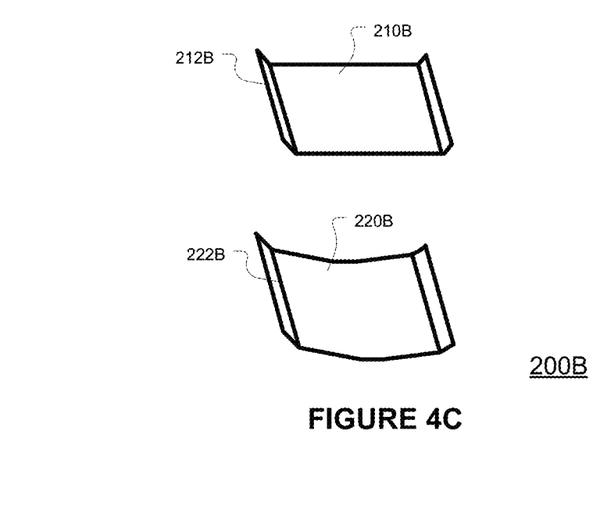
FIG. 4C is a simplified isometric drawing of top section and bottom section of a fixed custom interbody implant with shortened arms according to various embodiments.
Figure 5A:
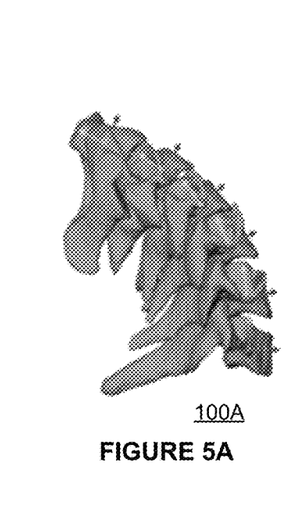
FIGS. 5A-5E are simplified, lateral view drawings of a plurality of cervical vertebrae in different states of movement including extension and flexion according to various embodiments.
Figure 5B:
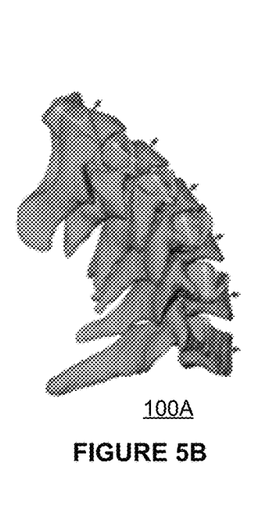
Figure 5C:
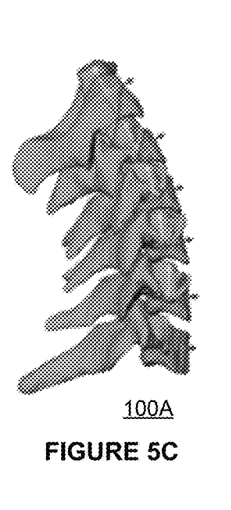
Figure 5D:
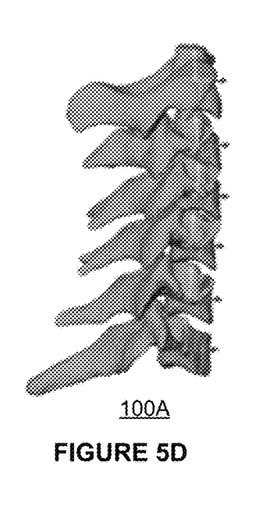
Figure 5E:
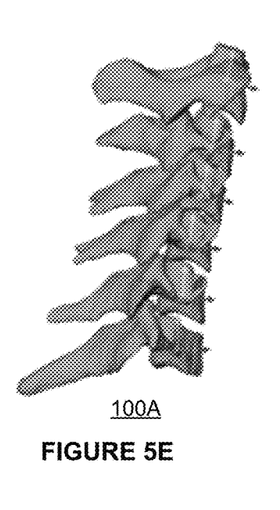
Figure 6A:
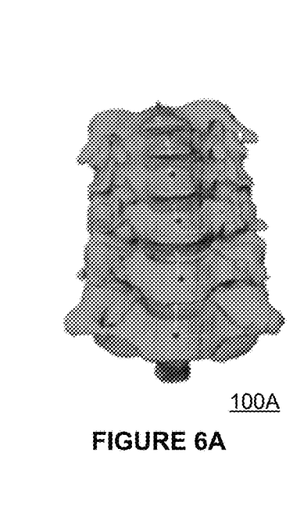
FIGS. 6A-6E are simplified, anterior view drawings of a plurality of cervical vertebrae in different states of movement including extension, flexion, and lateral flexion according to various embodiments.
Figure 6B:
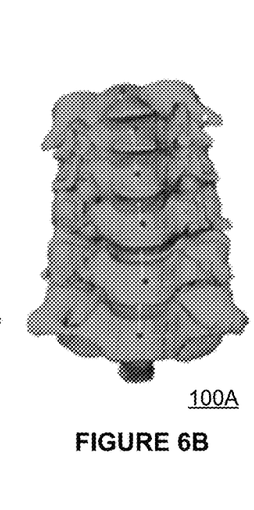
Figure 6C:
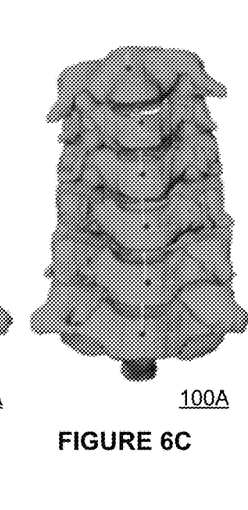
Figure 6D:
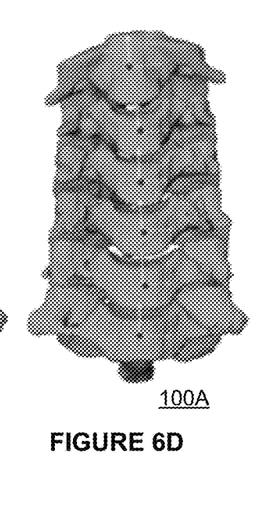
Figure 6E:
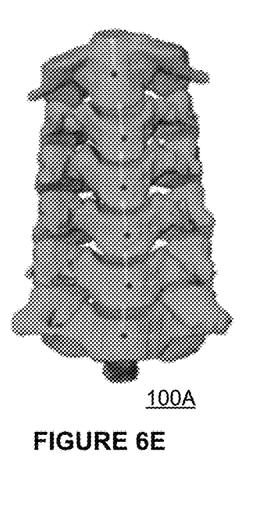

FIG. 4A is an enlarged image of area BB of FIG. 2A with another simplified drawing of a fixed (non-moveable) custom interbody implant 200B with shorter arms 212B, 222B according to various embodiments. FIG. 4B is a simplified isometric drawing of the fixed custom interbody implant 200B with shorter arms 212B, 222B according to various embodiments. FIG. 4C is a simplified isometric drawing of top section 210B and bottom section 220B of a fixed custom interbody implant 200B with shorter arms 212A, 222A according to various embodiments. As shown in FIG. 4A, the interbody implant 200B may also be sized to fit securely and precisely into the region formed between two, adjacent cervical vertebrae 10A, 10B for a predetermined relationship or position between them. In an embodiment, the predetermined relationship may a neutral position between the bony elements 10A, 10B. In an embodiment, the predetermined position may be non-neutral to correct various anatomical issues for the respective adjacent bony elements 10A, 10B. The implants 200B shorter arms 212B may also engage the arms 18A, 18B of an inferior vertebrae 10A saddle 18 (upper region) and the sides 22A, 22B of a superior vertebrae 10B lower region 22 in an embodiment.

In an embodiment, a 4-D model of region(s) to be stabilized may be formed and used to produce a fixed custom interbody implant where a practitioner selects the desired range of motion by selecting a plurality of predetermined relationships between the bony elements 10A, 10B to be stabilized. In an embodiment, a 4-D model of region(s) to be stabilized may be generated by placing the bony segments 10 forming the region(s) in various the plurality of predetermined positions or relationships (activity 314 and FIGS. 5A-5A and 6A-6E in an embodiment) and mapping the region formed by the adjacent bony segments 10A, 10B in one of the plurality of predetermined positions or relationships (activity 316). When a desired number of regions form via various positions are mapped (such as determined by a surgeon, doctor, or other medical professional) (activity 318), a moveable custom implant 200C (implant that enables desired movement between bony segments) (FIGS. 7A-7C) may be formed based on the resultant 4-D models.

Figure 7A:
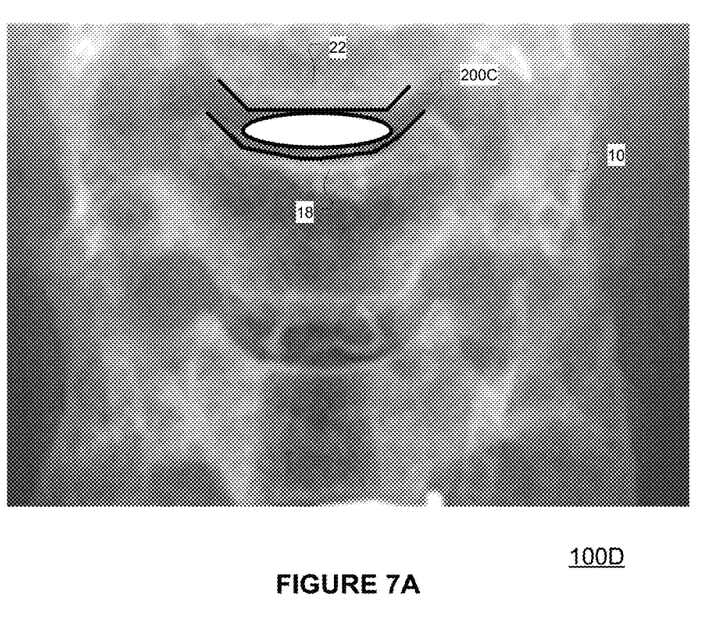
FIG. 7A is an enlarged x-ray image of area BB of FIG. 2A with a simplified drawing of a moveable custom interbody implant with elongated arms according to various embodiments.
Figure 7B:
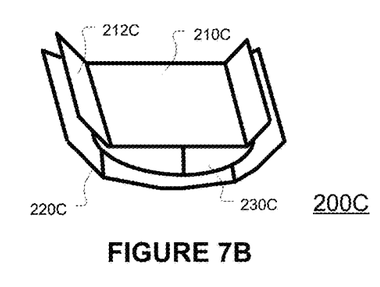
FIG. 7B is a simplified isometric drawing of a moveable custom interbody implant with elongated arms according to various embodiments.
Figure 7C:
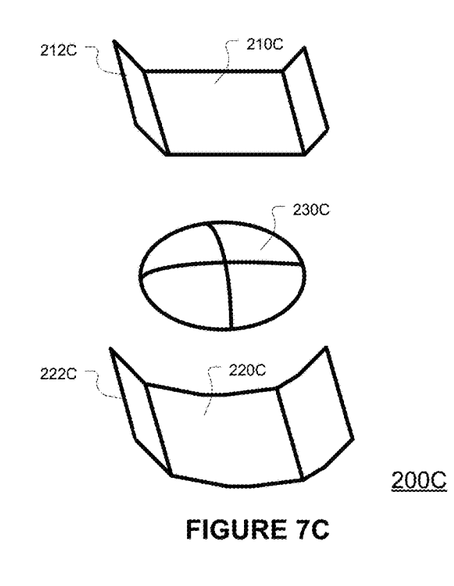
FIG. 7C is a simplified isometric drawing of a top section, a bottom section, and an articulation section of a moveable custom interbody implant with elongated arms according to various embodiments.

In an embodiment, portions of the moveable custom interbody implant 200C may be formed based on a selected predetermined position (activity 322). In an embodiment, the predetermined relationship may a neutral position between the bony elements 10A, 10B. In an embodiment, the predetermined position may be non-neutral to correct various anatomical issues for the respective adjacent bony elements 10A, 10B. The articulating areas, sections, or shapes, such as interface 230 may be formed based on the 4-D mappings for the region (activity 324) in an embodiment. In an embodiment, the interface 230 may formed of different materials than the top section 210C and bottom section 220C. The moveable custom interbody implant 200C may also have various arms lengths (if any) 212C, 222C in an embodiment.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus, the following claims are hereby incorporated into the Detailed Description, with each claim standing on its own as a separate embodiment.

What is claimed is:

1. An interbody implant for stabilizing adjacent bony elements when placed therebetween, the implant including:
   an upper face shaped to engage a lower region of a superior bony element of the adjacent bony elements when placed therebetween; and
   a lower face shaped to engage an upper region of an inferior bony element of the adjacent bony elements when placed therebetween,
   wherein the upper face and the lower face are shaped from a plurality of images taken of a region between the adjacent bony elements when the adjacent bony elements are placed in a first predetermined relationship to each other; and
   wherein the upper face is movably coupled to the lower face to form a movable relationship between the adjacent bony elements when placed therebetween based on the plurality of images taken of the region between the adjacent cervical vertebrae when the adjacent bony elements are placed in a plurality of predetermined relationships to each other.

2. The interbody implant of claim 1, wherein the adjacent bony elements are adjacent cervical vertebrae and the interbody implant is shaped to be placed in a disc space between the adjacent cervical vertebrae.

3. The interbody implant of claim 2, where the first predetermined relationship is a non-neutral relationship selected to address an anatomical condition between the adjacent cervical vertebrae.

4. The interbody implant of claim 2, wherein the upper face has arms that are shaped to extend partially beyond the disc space between the adjacent cervical vertebrae when placed therebetween and has an inverted saddle shape.

5. The interbody implant of claim 4, wherein the lower face has arms that are shaped to extend partially beyond the disc space between the adjacent cervical vertebrae when placed therebetween and has an inverted saddle shape.

6. The interbody implant of claim 2, wherein the upper face has arms that are shaped to extend beyond the disc space between the adjacent cervical vertebrae when placed therebetween and has an inverted saddle shape.

7. The interbody implant of claim 6, wherein the lower face has arms that are shaped to extend beyond the disc space between the adjacent cervical vertebrae when placed therebetween and has an inverted saddle shape.

8. The interbody implant of claim 7, wherein the upper face is fixably coupled to the lower face to form a nonmovable relationship between the adjacent cervical vertebrae when placed therebetween.

9. The interbody implant of claim 1, wherein the first predetermined relationship is a neutral relationship.

10. The interbody implant of claim 1, wherein the upper face is fixably coupled to the lower face to form a nonmovable relationship between the adjacent bony elements when placed therebetween.

11. The interbody implant of claim 1, wherein the upper face is movably coupled to the lower face to form a movable relationship between the adjacent bony elements when placed therebetween.

12. The interbody implant of claim 11, wherein the plurality of predetermined relationships are selected to provide a desired level of mobility between the adjacent cervical vertebrae when placed therebetween.

13. The interbody implant of claim 12, wherein the plurality of predetermined relationships are selected to provide a desired level of extension and flexion between the adjacent cervical vertebrae when placed therebetween.

14. The interbody implant of claim 12, wherein the plurality of predetermined relationships are selected to provide a desired level of extension, flexion, lateral flexion, and rotation between the adjacent cervical vertebrae when placed therebetween.

15. The interbody implant of claim 14, wherein the upper face has arms that are shaped to extend partially beyond the disc space between the adjacent cervical vertebrae when placed therebetween and has an inverted saddle shape.

16. The interbody implant of claim 15, wherein the lower face has arms that are shaped to extend partially beyond the disc space between the adjacent cervical vertebrae when placed therebetween and has an inverted saddle shape.

17. The interbody implant of claim 14, wherein the upper face has arms that are shaped to extend beyond the disc space between the adjacent cervical vertebrae when placed therebetween and has an inverted saddle shape.

18. The interbody implant of claim 17, wherein the lower face has arms that are shaped to extend beyond the disc space between the adjacent cervical vertebrae when placed therebetween and has an inverted saddle shape.

19. The interbody implant of claim 1, wherein the upper face is movably coupled to the lower face to form a movable relationship between the adjacent bony elements when placed therebetween based on the plurality of images taken of the region between the adjacent bony elements when the adjacent bony elements are placed in the plurality of predetermined relationships to each other.

* * * * *